(12) United States Patent
Deffenbaugh et al.

(10) Patent No.: US 8,998,969 B2
(45) Date of Patent: Apr. 7, 2015

(54) FASTENING SYSTEM FOR INTERNAL FIXATION

(71) Applicant: Biomet Manufacturing, LLC, Warsaw, IN (US)

(72) Inventors: Daren L. Deffenbaugh, Winona Lake, IN (US); Dale R. Schulze, Springboro, OH (US)

(73) Assignee: Biomet C.V., Gibraltar (GI)

( * ) Notice: Subject to any disclaimer, the term of this patent is extended or adjusted under 35 U.S.C. 154(b) by 0 days.

(21) Appl. No.: 14/093,931

(22) Filed: Dec. 2, 2013

(65) Prior Publication Data

US 2014/0081343 A1  Mar. 20, 2014

Related U.S. Application Data

(60) Continuation of application No. 12/952,031, filed on Nov. 22, 2010, now Pat. No. 8,597,300, which is a division of application No. 11/389,392, filed on Mar. 24, 2006, now Pat. No. 7,837,717.

(51) Int. Cl.
*A61B 17/68* (2006.01)
*A61B 17/80* (2006.01)
(Continued)

(52) U.S. Cl.
CPC .......... *A61B 17/683* (2013.01); *A61B 17/1735* (2013.01); *A61B 17/686* (2013.01); *A61B 17/80* (2013.01); *A61B 17/88* (2013.01);
(Continued)

(58) Field of Classification Search
USPC ........ 24/115 M, 115 R, 122.6, 135 R, 136 B, 24/136 M; 606/70–71, 86 B, 86 R, 96, 606/103–105, 139, 266, 279–299, 300–301, 606/304–306, 309, 314, 323–324, 328–329, 606/915–916
See application file for complete search history.

(56) References Cited

U.S. PATENT DOCUMENTS 2,294,398 A  9/1942  Ferguson
2,485,531 A  10/1949  Dzus et al.
(Continued)

FOREIGN PATENT DOCUMENTS

AT  389044 B  10/1989
DE  532436 C  8/1931
(Continued)

OTHER PUBLICATIONS

Japan Patent Office, Notification of Reasons for Refusal (Translation) associated with JP patent application (i.e., JP 2007-077338, mailed Feb. 28, 2012 (2 pages).

*Primary Examiner* — Larry E Waggle, Jr.
(74) *Attorney, Agent, or Firm* — Harness, Dickey (57) ABSTRACT

A bone fracture fixation system comprises a bone plate configured to bear against a proximal surface of the bone and a plurality of elongated tension elements, each sized to pass through an opening in the bone plate and through the bone from the proximal surface to a distal surface thereof. Each tension element is anchored to the bone and maintained in tension by a distal anchor attached to said tension element and configured to engage the distal surface of the bone and a proximal anchor engageable between the bone plate and the tension element. In one method for fixation of a bone fracture, the bone plate is positioned on a proximal surface of the bone while the tension element is introduced into the bone and through an opening in the bone plate from an opposite distal surface of the bone.

14 Claims, 8 Drawing Sheets

(51) Int. Cl.
*A61B 17/88* (2006.01)
*A61B 17/17* (2006.01)
*A61B 17/00* (2006.01)
*A61B 19/00* (2006.01)

(52) U.S. Cl.
CPC .. *A61B 17/8875* (2013.01); *A61B 2017/00867* (2013.01); *A61B 2019/464* (2013.01); *Y10S 606/916* (2013.01)

(56) References Cited

U.S. PATENT DOCUMENTS

| | | |
|---|---|---|
| 3,489,143 A | 1/1970 | Halloran |
| 4,946,462 A | 8/1990 | Watanabe |
| 5,190,545 A | 3/1993 | Corsi et al. |
| 5,234,435 A | 8/1993 | Seagrave, Jr. |
| 5,312,410 A | 5/1994 | Miller et al. |
| 5,607,430 A | 3/1997 | Bailey |
| 5,611,801 A | 3/1997 | Songer |
| 5,665,088 A | 9/1997 | Gil et al. |
| 5,665,089 A | 9/1997 | Dall et al. |
| 5,667,513 A | 9/1997 | Torrie et al. |
| 5,741,259 A | 4/1998 | Chan |
| 5,797,913 A | 8/1998 | Dambreville et al. |
| 5,797,916 A | 8/1998 | McDowell |
| 5,802,788 A | 9/1998 | Ozawa et al. |
| 5,810,824 A | 9/1998 | Chan |
| 5,921,986 A | 7/1999 | Bonutti |
| 5,931,839 A | 8/1999 | Medoff |
| 5,938,686 A | 8/1999 | Benderev et al. |
| 5,954,722 A | 9/1999 | Bono |
| 5,997,541 A | 12/1999 | Schenk |
| 6,019,762 A | 2/2000 | Cole |
| 6,068,648 A | 5/2000 | Cole et al. |
| 6,302,887 B1 | 10/2001 | Spranza et al. |
| 6,364,885 B1 | 4/2002 | Kilpela et al. |
| 6,368,326 B1 | 4/2002 | Dakin et al. |
| 6,520,965 B2 | 2/2003 | Chervitz et al. |
| 6,595,994 B2 | 7/2003 | Kilpela et al. |
| 6,764,513 B1 | 7/2004 | Dowling |
| 6,960,213 B2 | 11/2005 | Chervitz et al. |
| 7,578,825 B2 | 8/2009 | Huebner |
| 7,753,914 B2 * | 7/2010 | Ruhling et al. ............... 606/102 |
| 2001/0010005 A1 | 7/2001 | Kammerer et al. |
| 2002/0032432 A1 | 3/2002 | Nash et al. |
| 2002/0077631 A1 | 6/2002 | Lubbers et al. |
| 2002/0091391 A1 | 7/2002 | Cole et al. |
| 2005/0043734 A1 | 2/2005 | Kay |
| 2005/0049599 A1 | 3/2005 | Nesper et al. |
| 2005/0234472 A1 * | 10/2005 | Huebner ...................... 606/104 |

FOREIGN PATENT DOCUMENTS

| | | |
|---|---|---|
| DE | 748484 C | 11/1944 |
| WO | WO-0178615 A1 | 10/2001 |

* cited by examiner

FASTENING SYSTEM FOR INTERNAL FIXATION

CROSS-REFERENCE TO RELATED APPLICATIONS

This application is a continuation of U.S. patent application Ser. No. 12/952,031, filed on Nov. 22, 2010, now issued as U.S. Pat. No. 8,597,300, which is a divisional of application Ser. No. 11/389,392, filed Mar. 24, 2006, now issued as U.S. Pat. No. 7,837,717. The entire disclosures of each of the above applications are incorporated herein by reference.

BACKGROUND

The present invention relates to a system for internal fixation of a bone, and especially for the fixation of fractures of the bone.

For any bone fracture, the orthopaedic specialist must first reduce the fracture and then adequately stabilize and fix the bone to maintain the reduction as the bone heals. Each of these steps is complicated when the bone has suffered multiple fractures or a fracture that is not simply transverse. Fractures of this type usually require some form of internal fixation to reduce and maintain the bone fragments. One conventional approach to reducing bone fragments is with a bone plate extending over a portion of the bone at the fracture site. In one surgical approach, an orthopaedic surgeon may use a specialized clamp applied across the bone while attaching the fixation plate to the bone by screwing a plurality of screw fasteners through holes in the plate into the underlying bone.

Generally, screw fasteners are effective in holding the bone plate tightly against the healthy bone so that fracture may heal properly. However, in less healthy (e.g., osteopenic) bone, the screw threads may not find adequate purchase in the bone to hold the bone and plate together in proper alignment. This may result in non-union of the fracture that may require more invasive revision surgery to correct.

Another problem associated with screw fasteners is occasional breakage of the screw near the plate-bone interface due to stress concentrations arising from poor load sharing among all of the screws and/or high cyclic loading.

A further drawback of the screw fastener approach to internal fixation is that a large variety of screw sizes must be made available for each surgical procedure in order to accommodate variations in patient anatomy and fracture type. Maintaining a large inventory of screw sizes, along with the appropriately sized drills, guides, drivers and fixtures, can be costly. There is also the chance that an inappropriately sized screw may be selected during a procedure.

Fixation approaches have been developed that do not rely upon screw fasteners. For example, cerclage systems utilize one or more cables tightened around a bone to hold the fracture fragments together. The cable construct may include a plate that helps anchor the cables. However, cerclage systems require access around the entire periphery of the bone so it is necessary for the surgeon to dissect soft tissues surrounding the bone. Another problem is that the cerclage cable can exert significant line pressure against the periosteum, which may injure the bone and inhibit healing.

Accordingly, there is a need for a fracture fixation system that provides a stable construct in osteopenic bone and that may be adapted for minimally invasive surgical procedures. There is also a need for a fracture fixation system that reduces the inventory of fasteners and associated instrumentation required during the surgical procedure. There is a further need for a fracture fixation system that assists in improving and maintaining the fracture reduction during application and that incorporates fasteners that resist breakage after implantation and that are less technique sensitive to apply than conventional bone screws.

SUMMARY

In order to address these needs, the present invention provides a fracture fixation system that comprises a bone plate configured to bear against a proximal surface of the bone, the bone plate defining a plurality of openings therethrough. A plurality of elongated tension elements are provided, each sized to pass through one of the bone plate openings and through the bone from the proximal surface to a distal surface thereof. A distal anchor is attached to each tension element and configured to engage the distal surface of the bone when the tension element passes through the bone. A proximal anchor is engageable between the bone plate and each tension element to maintain tension in the tension element between the proximal anchor and the distal anchor. The tension element may be a braided metal cable or similar elongated element.

In one embodiment, the proximal anchor is a Tinnerman washer. In this embodiment, the bone plate defines a recess around at least some of the plurality of openings. The Tinnerman washer is sized to be received within the recess and is configured to engage the tension element passing therethrough to maintain tension on the element.

In other embodiments, the proximal anchor is configured for a polyaxial interface with the bone plate. With this feature, the tension element may be situated at a range of angles relative to the bone plate to optimize the ability of the surgeon to reduce multiple bone fracture fragments. In these embodiments, at least some of the openings define a spherical wall and include a locking bushing disposed therein. The locking bushing has a spherical outer surface for complementary engagement with the spherical wall, and further includes an internally threaded bore. The proximal anchor includes a central bore for receiving the tension element therethrough and a threaded head. The head of the anchor and the locking bushing define a tapered threaded interface so that the bushing expands into the spherical wall as the head is threaded into the bushing.

In one aspect, the distal anchor has a shape memory component with a first configuration sized to pass through the bone plate openings and through the bone from the proximal surface to a distal surface thereof. The shape memory component has a second shape memory configuration for engaging the distal surface of the bone. In one embodiment, the distal anchor includes at least two prongs that are substantially aligned with the elongated tension element in the first configuration and extended outward therefrom in the second shape memory configuration. The prongs may be spring elements or may be formed of a shape memory metal.

In other embodiments, the distal anchor is a fixed shape component that is sized to bear against the distal surface of the bone. Thus, the distal anchor may be a disc or a generally spherical element. In specific embodiments, the distal anchor may also include a washer with a recess to receive the spherical element therein.

The present invention contemplates a method for fixation of a bone fracture that comprises positioning a bone plate on a proximal surface of the bone, the bone plate including a plurality of openings therethrough and passing at least two elongated tension elements through plate openings and through the bone to a distal surface thereof. Each tension elements is anchored to the distal surface of the bone and then placed in tension. The proximal end of the tension element is then anchored to the bone plate while maintaining the tension in the element. To facilitate passage of each tension element through the bone, a K-wire or stylet may be used to form an appropriately oriented path and a sheath may be used to help convey the tension element, and in some cases the distal anchor, through the bone.

In accordance with one embodiment of the invention, a tool is provided for use with a pair of elongated medical devices. The tool comprises a barrel defining an elongated bore open between a proximal end and a distal end that is sized to receive an elongated medical device at a corresponding one of the proximal and distal ends. The barrel further defines a first side opening communicating with the elongated bore extending from the proximal end toward the distal end, and a second side opening also communicating with the elongated bore but extending from the distal end toward the proximal end. The second side opening is angularly offset relative to the first side opening and is connected to the first side opening by an intermediate side opening defined in the barrel. The side openings are sized to permit removal of one of the elongated medical devices from the elongated bore.

The tool is used by introducing an end of one of the elongated medical devices into the proximal end of the barrel and an end of the other elongated medical device into the distal end of the barrel. The two ends of the elongated devices mate within the barrel so that the barrel can serve as a guide for advancement of the elongated medical devices therethrough. The tool can thus be used for positioning an elongated medical element within a bone.

In a further aspect of the invention a method for positioning the elongated medical device within a bone comprises extending a first elongated element through a bone so that a distal end of the first element extends outside the bone and then mating a proximal end of a second elongated element with the distal end of the first element. The tool may be used to perform this mating step.

In a further aspect of the method, the second elongated element is pushed into the bone while maintaining the proximal end and the distal end in mating contact. Once the proximal end of the second element has exited the bone, the first element may be removed. In certain embodiments of the invention, the second elongated element is a tension element used to reduce and fix a bone fracture.

In one aspect, elongated elements includes a recess and the other of the elements includes a tip adapted to be received within the recess. In a specific embodiment, the first element is a K-wire having a sharpened tip at its distal end, while the second element is a tension cable having a recess at its proximal end.

In a further embodiment of the invention, a method is provided for fixation of a bone fracture. This method comprises the steps of:

(a) providing a bone plate including a plurality of openings and positioning the bone plate on the surface of the bone;
(b) extending a first elongated element through the bone so that a distal end of the first element extends outside the bone;
(c) providing an elongated tension element having an anchor portion at a distal end thereof;
(d) mating a proximal end of the tension element with the distal end of the first element;
(e) pushing the tension element into the bone while maintaining the proximal end and the distal end in mating contact until the anchor portion of the tension element contacts the bone;
(f) removing the first element from the tension element when the proximal end of the second element exits the bone;
(g) extending the proximal end of the tension element through one of the openings in the bone plate;
(h) tensioning the tension element; and
(i) while maintaining the tension element in tension, anchoring the tension element to the bone plate.

In certain embodiments, the first elongated element is a K-wire having a sharpened tip, wherein the K-wire is driven through the bone by a drill. In the preferred embodiment, the bone plate is positioned on the bone prior to extending the first elongated element through the one of the openings in the plate. The bone plate may thus serve as a guide for orienting and positioning a second tension element within the bone.

In one aspect of the inventive method, the step of anchoring the tension element to the bone plate includes extending a cannulated drill over the proximal end of the tension element and forming a bore at least partially into the bone using the cannulated drill. A cannulated anchor element is advanced along the proximal end of the tension element, through an opening in the bone plate and into the bore formed in the bone.

The present invention contemplates that the method steps are repeated for a plurality of tension elements to effectively reduce bone fragments of the fracture. The step of anchoring all the tension elements to the bone plate may include adjusting the tension in selected ones of the tension elements prior to anchoring the selected tension elements. Once all of the tension elements have been properly tensioned and anchored to the bone plate, the excess portions of the elements are severed and removed.

One significant benefit of the fracture fixation system of the present invention is that it is well suited for use in soft, osteopenic bone that is otherwise incapable of supporting a lag screw. At the same time, the tension elements provide a lag effect for optimal fracture reduction.

Another benefit is that the tension elements and anchors may be provided as "one size fits all". In other words, once the tension elements are tensioned and anchored, any excess material is removed. The necessary size of the tension element need not be determined prior to implantation. The tension element may be arranged to pass directly across the bone or across long spans of the bone without requiring differently sized elements.

It is one important object of the invention to provide a fracture fixation system that is particularly well suited for use in reducing multiple fracture fragments. It is another object to provide a fixation system that can be used equally well with healthy or less than healthy bone. Other objects and benefits of the invention will become apparent upon consideration of the following written description along with the accompanying figures.

DRAWINGS

FIGS. 10a, 10b are side views of additional distal anchors of a distal anchor for use with the fracture fixation system shown in FIG. 1.

FIG. 11a is a side view of a tension element and distal anchor for use with the fracture fixation system shown in FIG. 1, according to one embodiment of the invention.

FIG. 11b is an enlarged partial cross-sectional view of the proximal end of the tension element shown in FIG. 11a.

DETAILED DESCRIPTION

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 1:
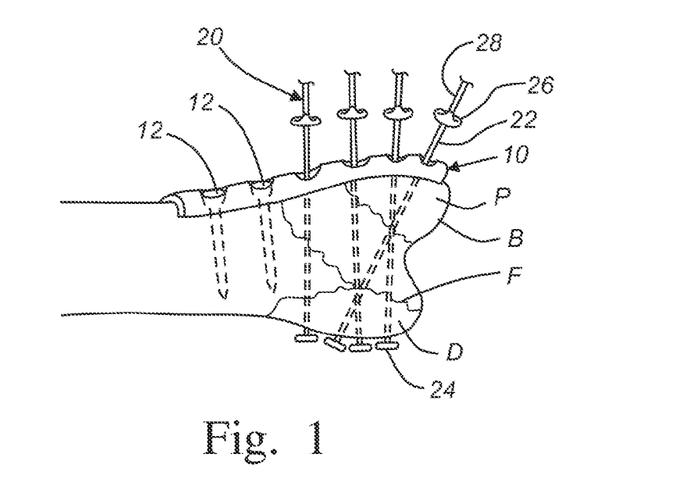
FIG. 1 is a side perspective of a fracture fixation system according to one embodiment of the present invention.
Figure 2:
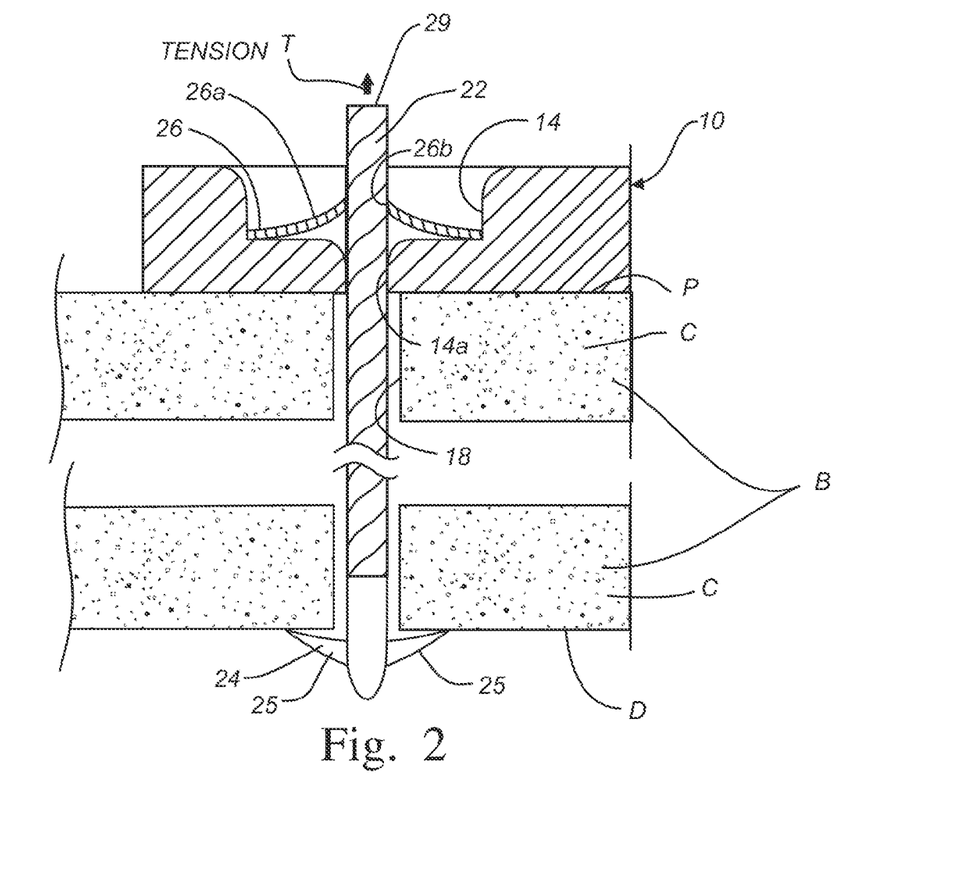
FIG. 2 is an enlarged cross-sectional view of a fracture fixation system according to another embodiment of the present invention.

The present invention contemplates a system for reducing and fixing bone fractures, such as the fractures F in bone B shown in FIG. 1. The present system is particularly suited for fractures with multiple bone fragments that require precise reduction and secure fixation to maintain the reduction as the bone mends. In accordance with one embodiment, a bone plate 10 is positioned on the bone in a conventional manner. The bone plate may be of many known configurations that incorporate a series of recesses (FIG. 2). In one embodiment, bone screws 12 may be used to anchor one end of the bone plate 10 away from the fractures F. These screws help anchor the fixation arrangement in viable bone and can also help hold the plate as other fixation elements are introduced into the bone.

In accordance with the present invention, it is contemplated that a fixation system 20 includes a plurality of tension elements 22 that are adapted to work with the plate 10 to reduce the fractures F in the bone B. The tension elements are configured to extend through the recess 14 and opening 14a in the bone plate 10 and through a bore 18 formed in the bone, as shown in FIG. 2. The tension elements 22 are therefor sized to span from a proximal surface P to an opposite distal surface D of the bone B. The distal end of the tension elements 22 is provided with a distal anchor 24 which may come in a variety of forms that are adapted to anchor against the cortical bone C at the distal surface D of the bone when tension is applied to the tension element 22. A proximal anchor 26 engages the proximal end of the tension element to the bone plate at the proximal surface P of the bone and is configured to hold tension in the tension element 22.

The tension element 22 is an elongated flexible element that is capable of being pulled into tension and then anchored at its opposite ends. In certain embodiments, the tension element may be a braided metal cable, a monofilament or braided suture, or a biocompatible wire. When the fixation system 20 is initially installed, the tension element 22 includes an excess portion 28 that projects beyond the bone B and plate 10. Once the proximal anchor 26 is fixed, the excess portion 28 can be severed, leaving a cut end 29 that is preferably as close to the proximal surface P of the bone B as possible. The tension element can be severed using a tool appropriate for the particular material of the element.

In the embodiment illustrated in FIGS. 1-2, the proximal anchor 26 is a gripping washer, such as a Tinnerman washer. As is known in the art, a Tinnerman washer includes a conical central portion 26a having a central opening 26b. In accordance with the present invention, the central opening 26b has an effective diameter slightly less than the effective diameter of the tension element 22. As depicted in FIG. 2, the proximal anchor or washer 26 is positioned within the recess 14 in the plate 10 with the conical portion 26a projecting outward from the plate. With this orientation, the proximal anchor 26 can hold the tension in the element 22 since any pull opposite the tension direction T will tend to dig the element into the opening 26b and will try to compress the conical portion 26a. The walls of the recess 14 keep the washer 26 from flattening so that the washer will act to maintain the tension in the element 22 between distal and proximal anchors 24, 26.

Figure 3:
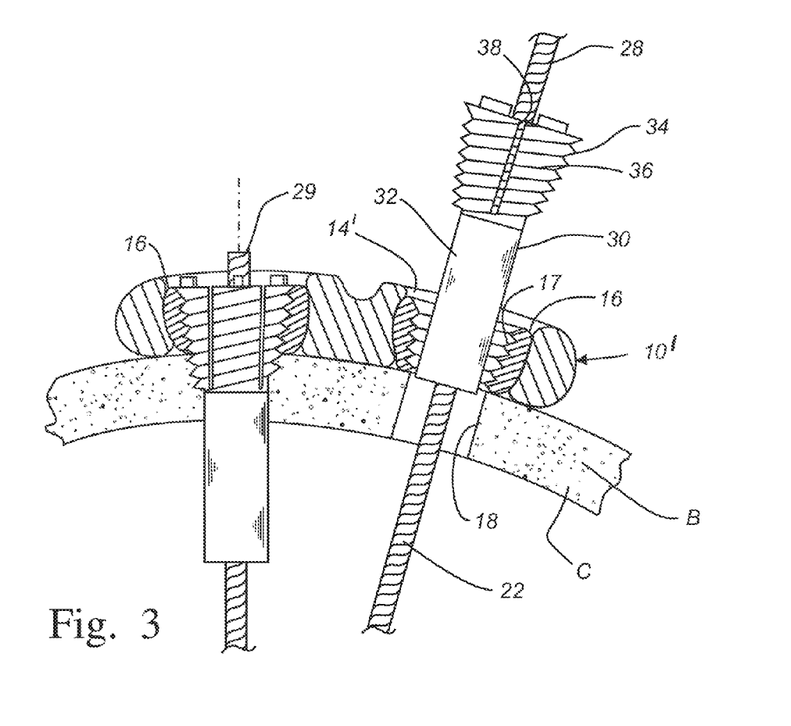
FIG. 3 is an enlarged cross-sectional view of a fracture fixation system according to a further embodiment of the invention.
Figure 4:
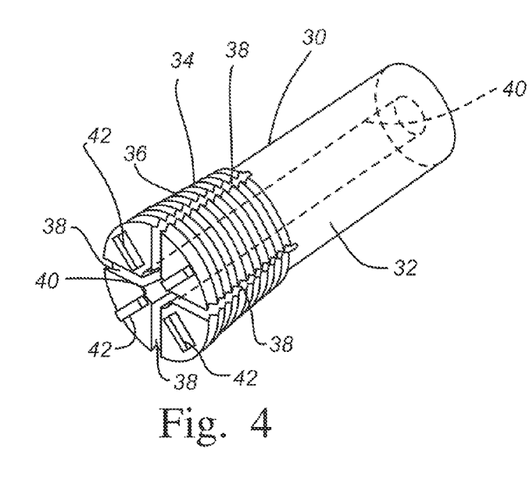
FIG. 4 is an enlarged perspective view of a proximal anchor used in the fracture fixation system shown in FIG. 3.

An alternative proximal anchor 30 is illustrated in FIGS. 3-4. This anchor is especially adapted for use with a bone plate 10' that is similar to the polyaxial locking plate disclosed in U.S. Pat. No. 5,954,722 (the '722 patent), the disclosure of which is incorporated herein by reference. This locking plate includes a plurality of thru-holes 14' in which the wall of the holes is generally spherical. A locking bushing 16 similar to the bushing disclosed in the '722 patent is configured to fit within the spherical walls of the thru-holes 14' so that the bushing can assume a range of angular orientations relative to the plate 10'. The bushing 16 is provided with internal threads 17. As disclosed in the '722 patent, the locking bushing is configured to receive the tapered threaded head of a bone screw so that as the head is threaded into the internal threads 17 the bushing 16 expands outwardly into the spherical surface of the thru-bore 14' to lock the bushing, and hence the bone screw, at the particular angular orientation relative to the locking plate.

The proximal anchor 30 of this embodiment includes a non-threaded shank 32 that is configured to extend through the plate 10' and into the bone bore 18 in the bone B. In one specific embodiment, the shank 32 may be tapered to form a press-fit engagement within the cortical bone C near the proximal surface P of the bone B. The proximal anchor 30 further includes a tapered head 34 that carries external threads 36 for engaging the internal threads 17 of the locking bushing 16. Like the bone screw in the '722 patent, the tapered head 34 of the proximal anchor 30 expands the bushing as the head is threaded into the bushing, thereby locking the bushing within the spherical walls of the thru-hole 14' in the plate 10'. Thus, as with the bone screw in the '722 patent, the proximal anchor 30 incorporates a polyaxial capability that allows the anchor to assume a range of angular orientations relative to the bone plate 10'. This polyaxial capability allows the tension element 22 passing through the anchor 30 to assume a comparable range of angles relative to the plate when the element is tensioned and anchored. Thus, it can be seen that the polyaxial capability enhances a surgeon's ability to reduce difficult bone fragments and hold that reduction over time.

As seen in FIG. 4, the proximal anchor 30 defines a central bore 40 through which the tension element 22 extends, as depicted in FIG. 22. In order to provide a clamping effect on the tension element, the anchor 30 further defines an array of cross-slots 38 passing through the central bore 40. As the head portion 34 is threaded into the locking bushing 16, the cross-slots 38 allow the effective diameter of the central bore 40 to decrease, thereby compressing about the tension element. As with the Tinnerman washer 26 discussed above, any pulling force on the tension element 22 will tend to pull the head 34 of the proximal anchor 30 deeper into the bushing 16, which has the effect of further closing the cross-slots and central bore around the tension element. Thus, the head portion 34 of the proximal anchor accomplishes two locking functions—first, locking the angular orientation of the anchor relative to the plate, and second, locking the tension element within the anchor.

In one specific embodiment, the head portion 34 defines driving lugs 42 on the proximal face thereof. A driving tool, such as the tool 50 shown in FIG. 5, may engage the lugs to permit rotation of the proximal anchor. The driving tool 50 is cannulated 52 with drive slots 54 configured to tightly engage the lugs 42 on the proximal anchor. The cannulated aspect of the tool 50 allows the tool to be used to drive the proximal anchor into the bone plate 10' while the excess portion 28 of the tension element is still available for tensioning the element.

In a method of using the fixation system 20 of the present invention, a bone plate 10, 10' is positioned on the bone B so that the plate openings 14a, 14' are optimally oriented for reducing the bone fragments of the fracture F. One end of the bone plate may be anchored to the bone B using fasteners, such as the screws 12 shown in FIG. 1. A drill guide is then mounted over a plate opening and an orthopaedic drill is used to form the bone bore 18 through the bone B, exiting at the distal surface D. A K-wire may be first inserted to help guide the bone drill. The bone bore 18 is preferably sized slightly larger than the effective diameter of the tension element 22. In the embodiment of the fixation system that uses the proximal anchors 30, a larger diameter bone bore 18 may be formed in the proximal cortical bone C for engagement by the shank 32 of the anchor, as depicted in FIG. 3.

Figure 5:
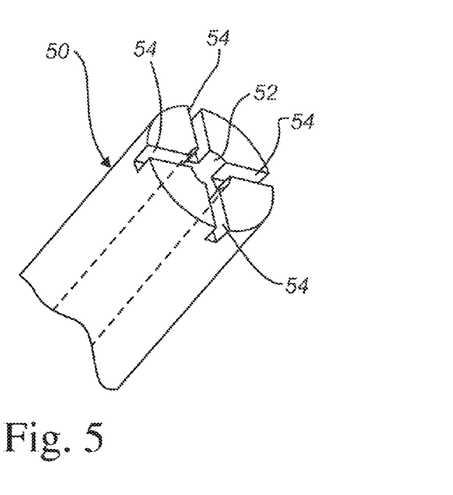
FIG. 5 is an enlarged perspective partial view of the working end of a driving tool for driving the proximal anchor shown in FIG. 4.

Once the bone bore 18 has been formed, a tension element 22 is passed through the plate opening and bone bore until the distal anchor 24 has exited at the distal surface D of the bone. In certain embodiments, an introducer sheath (not shown) may be first positioned within the bone bore 18 to facilitate passage of the tension element. With the distal anchor 24 in position, the proximal anchor 26 or 30 is threaded onto the proximal end of the tension element. Tension may be applied to the tension element by pulling at the excess portion 28 of the element 22. A cable tensioning device, such as the device disclosed in U.S. Pat. No. 6,595,994 (the '994 patent), the disclosure of which is incorporated herein by reference, may be adapted to engage the tension element 22 and apply tension to the element in a manner that permits fixation of the element by the proximal anchor. In one approach, the working end of the device disclose din the '994 patent can bear against the proximal anchor Tinnerman washer 26 as the tension element or cable is pulled in the tension direction T (FIG. 2). In a further embodiment, the working end of the cable tensioning device in the '994 patent may be modified to bear against the proximal face of the anchor 30 (FIG. 4). Moreover, the working end of the tensioning device may be modified to incorporate the driving tool 50 (FIG. 5). In this further embodiment, once the appropriate tension has been applied to the element 22, the proximal anchor 30 may be tightened into the locking bushing 16 to fix the construct.

The distal anchor 24 is configured to engage the distal surface D of the bone B when tension is applied and maintained in the tension element 22. In one specific embodiment, the distal anchor may include wings 25 (FIG. 2) that pivot outward once the distal end has exited the bone bore 18 at the distal surface D. The wings may be propelled outward by a torsion spring disposed within the distal tip of the tension element.

In an alternative embodiment illustrated in FIGS. 6a-7b, the distal anchor incorporates shape memory technology. In this embodiment, a tension element 60 includes prongs 64 that exhibit shape memory to move to an expanded orientation 64' shown in FIG. 6b. This shape memory feature may be provided by pre-bending the distal end of the tension element 60 so that the prongs spring outward to the position shown in FIG. 6b. In order to introduce the tension element through the plate 10/10' and the bone bore 18, the element 60 is threaded into an introducer sheath 62 with the prongs maintained within the sheath as the sheath and tension element are passed through the bone plate and bone bore. Once the prongs 64 are positioned at the distal surface D of the bone, the sheath may be retracted, allowing the prongs to assume their anchoring configuration. One benefit of this shape memory feature is that the tension element may be removed by dislodging the distal anchor, which can advantageously be accomplished by extending the sheath 62 back along the tension element until it contacts the prongs and draw them inward within the sheath.

Figure 7A:
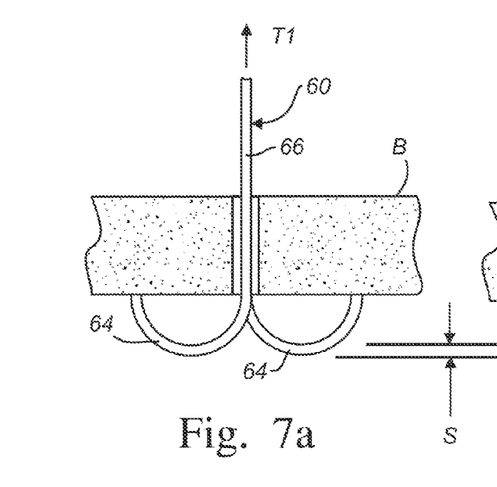
FIGS. 7a, 7b are side partial cross-sectional views of the distal anchor depicted in FIGS. 6a, 6b, shown with the distal anchor within a bone in its extended and tensioned states.
Figure 7B:
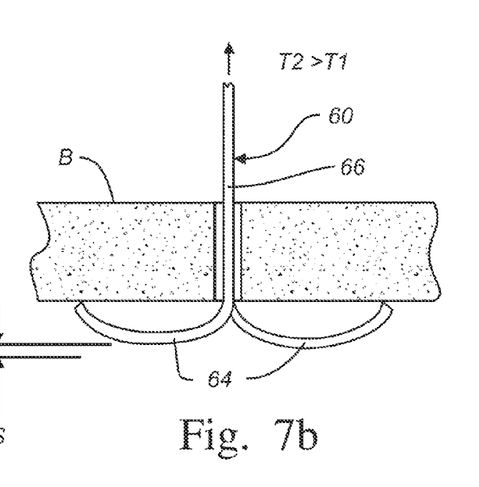
Figure 8A:
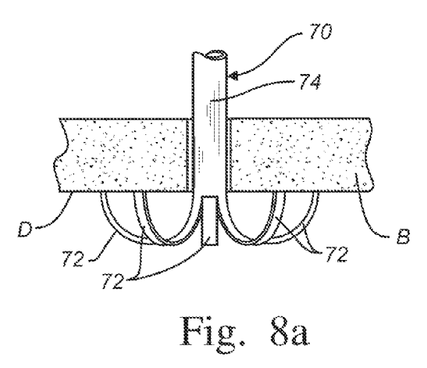
FIGS. 8a, 8b are side partial cross-sectional and bottom views of a distal anchor for use with the fracture fixation system shown in FIG. 1, according to a further embodiment of the invention.
Figure 8B:
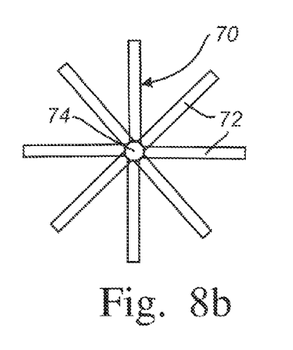
Figure 9:
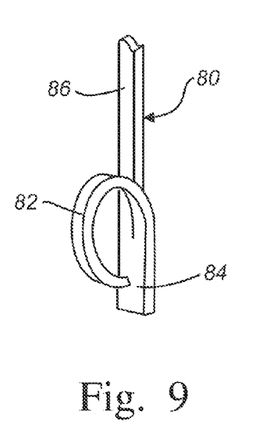
FIG. 9 is a side perspective view of a distal anchor for use with the fracture fixation system shown in FIG. 1, according to still another embodiment of the invention.

The tension element 60, and more particularly the shape memory prongs 64, may be configured to enhance their anchoring capability when the tension element 60 is tensioned. In particular, as illustrated in FIG. 7a, the tension element 60 may be positioned initially with the body 66 extending through the plate and bone and with the prongs 64 in an initial extended orientation. This initial orientation nominally corresponds to the free state of the shape memory prongs when left unconstrained. As tension is applied to the body 66, the prongs flatten from their initial orientation by a distance S. In this tensioned configuration the prongs 64 act as springs to increase the tension T2 in the body 66 from the original tension T1 (FIG. 7a). This characteristic of the tension element 60 may be used to control the amount of tension applied to the element and prevent over-tensioning. For instance, the "flatness" of the prongs may be gauged to provide an indication of the tension. It may also be contemplated that under excess tension the prongs 64 will invert and begin to move into the bone bore, which thus has the effect of dumping the tension in the element 60.

In one specific embodiment, the prongs 64 are formed of a spring material, such as medical grade spring steel. In another embodiment, the prongs are formed of a shape memory metal, such as NITINOL™. As is known in the art, a shape memory metal changes shape at a pre-determined temperature, which is typically near body temperature.

Figure 6A:
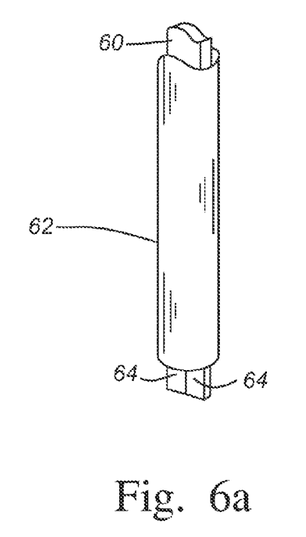
FIGS. 6a, 6b are side views of a distal anchor for use with the fracture fixation system shown in FIG. 1 according to one embodiment of the invention, with the distal anchor shown in its non-extended and extended states.
Figure 6B:
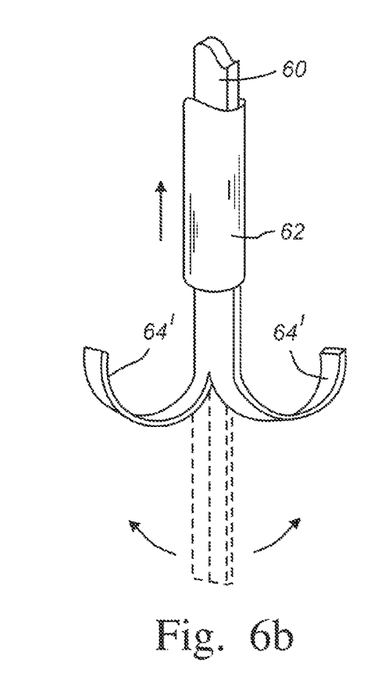

In the embodiment depicted in FIGS. 6a-6b, the tension element 60 includes a pair of opposite prongs 64. In another specific embodiment, a tension element 70 may include more than two prongs 72 extending from an elongated body 74. The multiple prongs 72 preferably exhibit the same shape memory characteristics as the prongs 64 described above. In yet another embodiment, a tension element 80 includes an elongated body 86 terminating in a distal portion 84. A curl element 82 separates from the distal portion 84 when the distal end is adjacent the distal surface D of the bone B. The curl element 82 may have a normal, unloaded radius of curvature, while the radius is reduced when tension is applied to the body 86. As the radius decreases, the curl element 82 exerts a greater resistance, thereby increasing the tension, as with the tension element 60 described above.

Figure 10A:
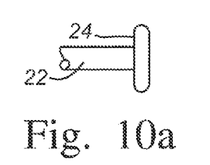

In other embodiments of the invention, the distal anchor may incorporate a fixed component. For instance, as shown in FIG. 10a, the tension element 22 terminates in a disc 24. In an alternative embodiment, the tension element 22 may terminate in a rounded element 24'. The rounded element 24' has one radius of curvature R1 and a larger radius of curvature R2 at the surface that contacts the soft tissue surrounding the bone in order to minimize the trauma to the adjacent tissue. The smaller radius R1 is configured to sit within a complementary configured recess 27a of a washer 27 that is disposed between the bone and the distal anchor. This washer/anchor interface permits variable angular orientations while ensuring uniform load distribution on the distal surface of the bone. In yet another specific embodiment, the distal anchor may constitute a spherical ball 92 fixed at the end of the body 94 of a tension element 90, as illustrated in FIG. 11a.

Figures 10B, 11A, 11B:
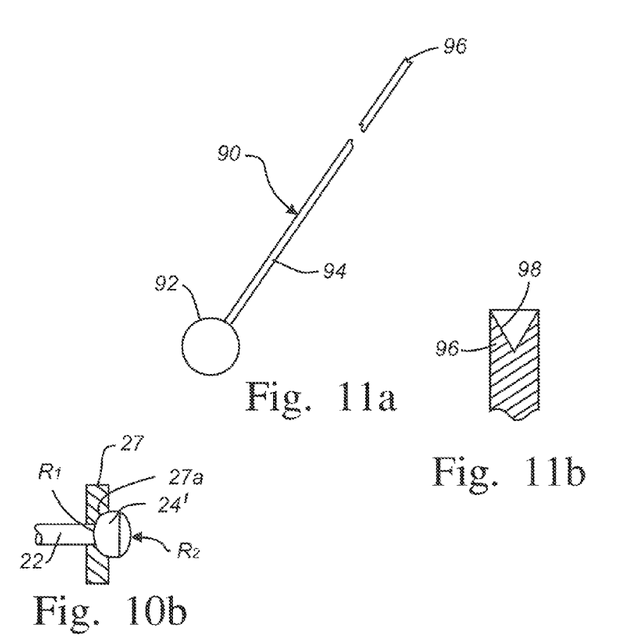

One common attribute of the embodiments shown in FIGS. 10a, 10b and 11a is that the distal anchors are, in effect, rigid, and incapable of passing through the plate opening 14/14' or the bone opening 18. Thus, unlike the shape memory anchors of FIGS. 6a-9, the tension elements with the distal anchors 24, 24' and 92 cannot be inserted from the proximal surface P of the bone B. A further embodiment of the invention contemplates a system and method for introducing these tension elements through the distal surface D to mate with a bone plate at the proximal surface P, all in a minimally invasive procedure.

Figure 12:
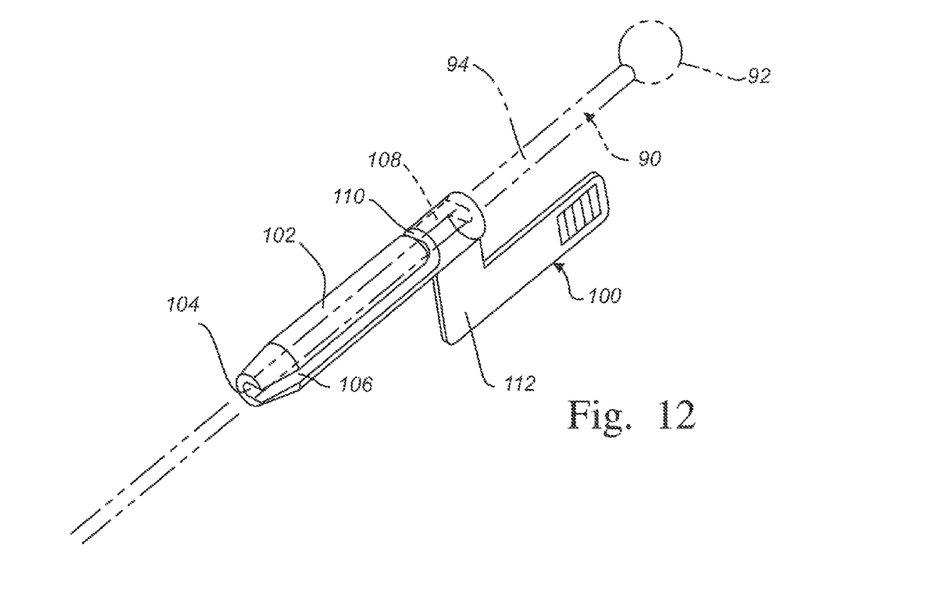
FIG. 12 is a perspective view of an exchange tool for use in a surgical procedure to fix the fixation system shown in FIG. 1 to a bone.
Figure 13A:
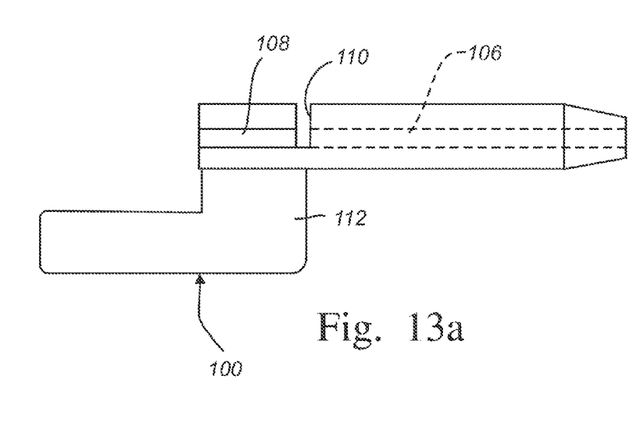
FIGS. 13a, 13b are side and end views of the exchange tool shown in FIG. 12.
Figure 13B:
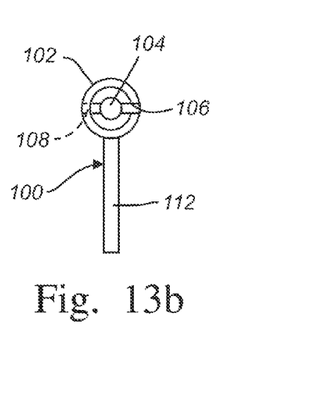

In this embodiment, an exchange tool 100 that is used to facilitate retrograde movement of the proximal end 96 of the tension element 90 through a bone bore. As shown in FIGS. 12, 13a and 13b, the tool 100 includes a barrel 102 that defines a bore 104 therethrough that is sized to receive the elongated body 94 of the tension element 90. The barrel 102 defines a side opening 106 at a proximal portion of the barrel and a distal side opening 108 at a distal portion. The distal side opening 108 is offset from the proximal side opening 106 although the two side openings are contiguous through a connecting slot 110. The tool 100 further includes a handle 112 connected to the barrel 102 that is used to manipulate the exchange tool as described below. As best seen in FIG. 13b, the two side openings 106 and 108 are preferably about 180° apart.

Figure 14:
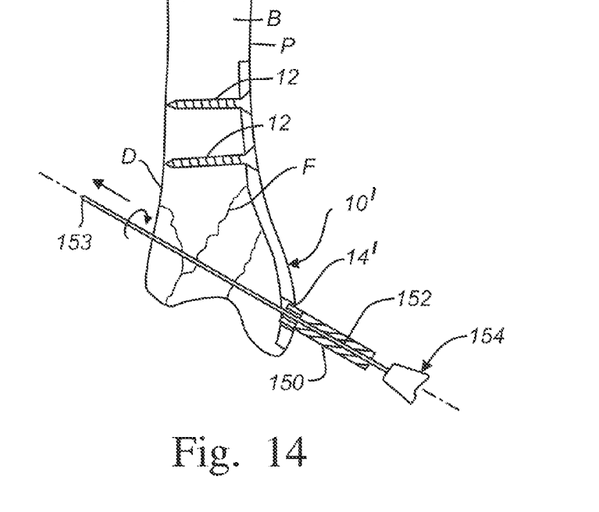
FIG. 14 is a representation of a first step in a method for fixing a fixation system as shown in FIG. 1 to reduce and fix a fractured bone, in accordance with one embodiment of the invention.

The exchange tool is used in the series of steps depicted in FIGS. 14-19. In a first step, a bone plate 10' is shaped to fit a bone B adjacent a fracture site F. As described above, the bone plate 10' may be anchored by bone screws 12 positioned apart from the fracture site. A guide 150 is positioned within a plate opening 14' that is aligned with a desired fixation location. It can be appreciated that a pattern of fixation may be pre-planned based on radiographic images of the bone fragments. As shown in FIG. 14, a first tension element may be introduced to span numerous fractures at the head of the bone B. The guide 150 is sized to receive a K-wire 152. The K-wire is operatively coupled to a drill 154 that is used to drive the K-wire through the bone at a desired angle relative to the plate 10'. In the above-described embodiments that utilize the shape memory feature, it is necessary to form the bone bore 18 so that the distal anchor may be conveyed through the bone. In the embodiment of FIGS. 14-19, it is not necessary to initially form the bone bore since the distal anchor will be introduced from the distal surface D of the bone.

The K-wire 152 has a sharpened tip 153 adapted to penetrate bone. Other similar devices may be used, such as a thin gauge stylet. In an alternative approach, a separate drill bit may be used to form a narrow bore through the bone, with the K-wire, stylet or similar elongated element advanced through the bore. In this alternative approach, the drilled bore preferably has a diameter smaller than the diameter of the K-wire or stylet.

Figures 15, 16:
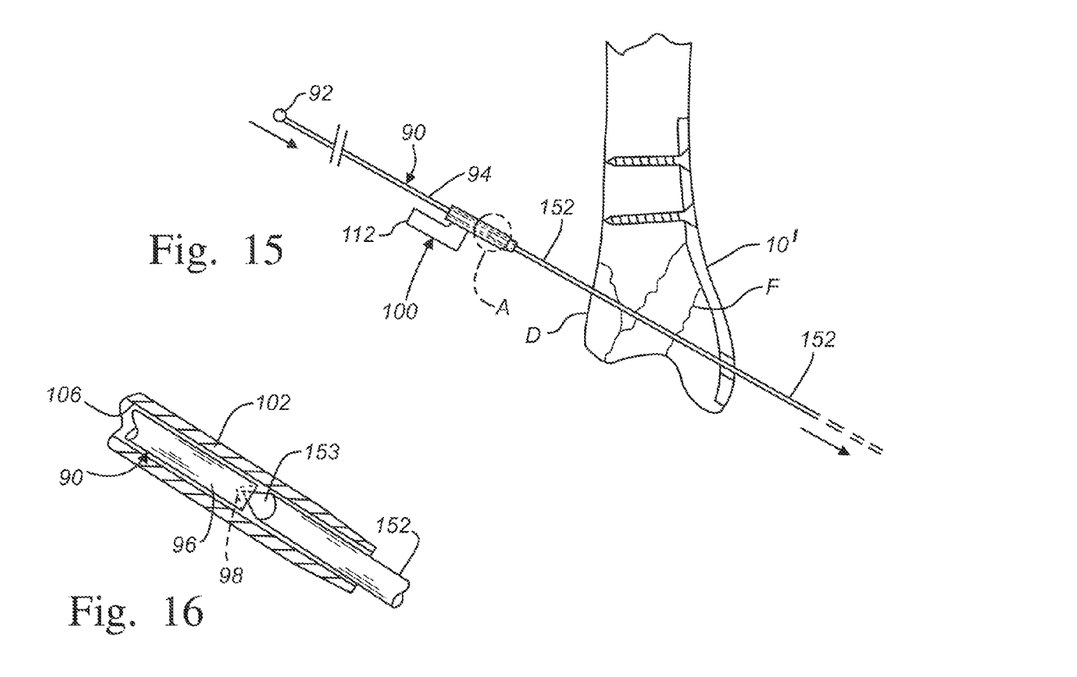
FIG. 15 is a representation of a further step in the method for fixing a fixation system to reduce and fix a fractured bone.
FIG. 16 is an enlarged partial cross-sectional view of the interface between a tension element and a K-wire, designated as area A in FIG. 15.
Figure 17:
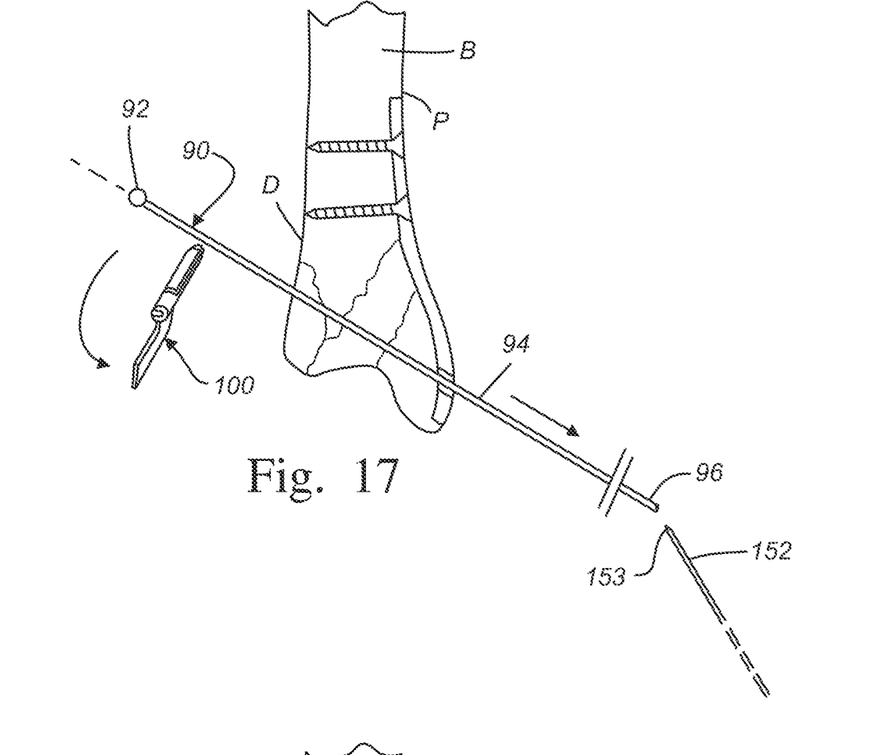
FIGS. 17-20 are representations of subsequent steps in the method for fixing a fixation system as shown in FIG. 1 in accordance with one embodiment of the invention.

Once the K-wire has exited the bone through the distal surface, the exchange tool 100 is positioned over the distal tip of the K-wire 152 so that the K-wire extends through the central bore 104, as shown in the detail view of FIG. 16. The proximal end 96 of the tension element 90 is then introduced into the bore 104 from the distal end of the tool 100. As shown in FIG. 11b, the proximal end 96 defines a conical recess 98. This recess is configured to accept the tapered tip 153 of the K-wire, as depicted in FIG. 16. It can thus be appreciated that the exchange tool 100 provides a mechanism for aligning the elongated body 94 of the tension element 90 with the K-wire 152 at the distal side of the bone B.

With the K-wire and tension element united within the exchange tool, the barrel 102 of the tool is preferably moved into contact with or at least immediately adjacent the distal surface D of the bone. The body 94 of the tension element 90 is then pushed retrograde toward the bone B, as shown in FIG. 15. As the tension element moves toward the bone, the proximal end 96 pushes the K-wire 152 out of the bone. It can be appreciated that once the K-wire/tension element interface reaches the bone B, the exchange tool 100 is no longer required to maintain that interface. Thus, the tool may be readily removed by rotating the tool in the direction of the arrow in FIG. 17 so that the tool essentially pivots about the connecting slot 110. As the tool is pivoted, the elongated body 94 of the tension element automatically exits the central bore 104 through the side slots 106, 108, leaving only a portion of the body 94 within the connecting slot 110. The exchange tool 100 is then completely removed by sliding the connecting slot 110 off the tension element.

With the exchange tool removed, the bore formed in the bone by the introduction of the K-wire serves to guide the tension element 90 toward the proximal surface P of the bone. Eventually the tip 153 of the K-wire exits the bone at the proximal surface P and the K-wire can be removed. The tension element is then advanced farther through the bone until the distal anchor 92 contacts the distal surface D of the bone.

It can be appreciated that the exchange tool initially and the bore in the bone subsequently help maintain the tension element 90 in alignment. The central bore 104 in the exchange tool and the bone bore are only slightly greater in diameter than the body 94 of the tension element so the body cannot flex or buckle as the tension element is moved retrograde into and through the bone. Thus, even if the tension element exhibits lateral flexibility, it can still be advanced into the bone in the manner described.

Figure 18:
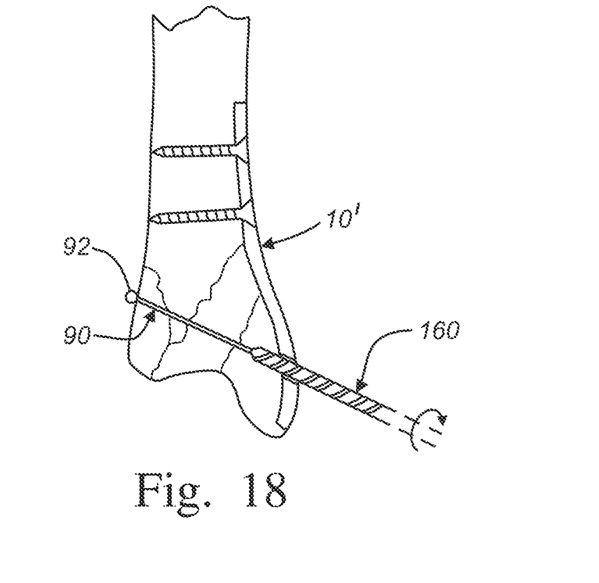
Figure 19:
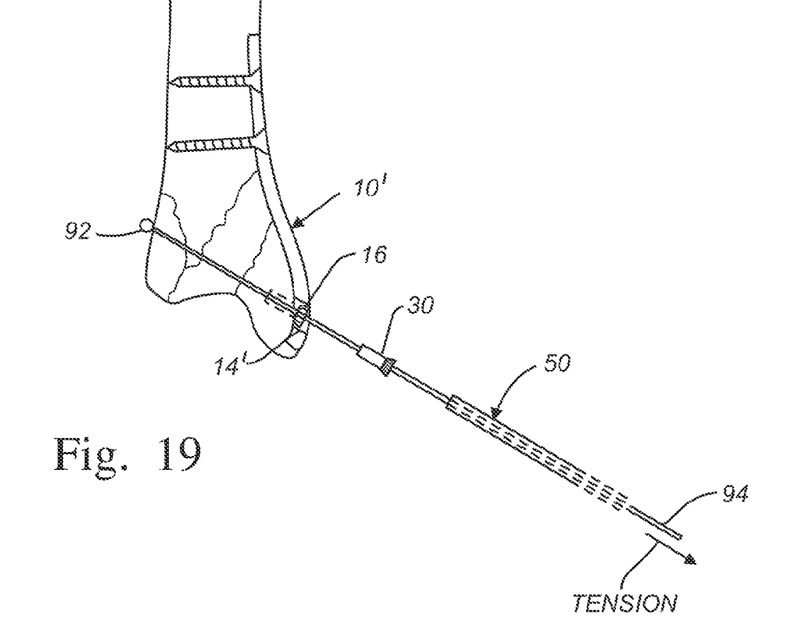
Figure 20:
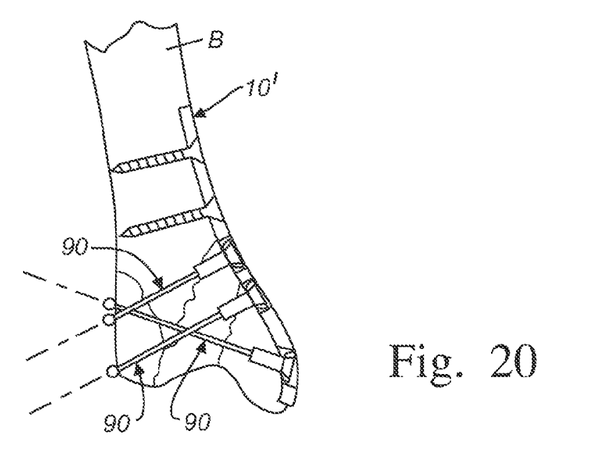

At this point, the tension element 90 is available to receive a proximal anchor to reduce the fracture and fix the tension element to the bone plate. In the case of the anchor 26 shown in FIGS. 1-2, the Tinnerman washer may be threaded onto the exposed portion of the tension element and tightened as described above. For the anchor 30 shown in FIGS. 3-4, the next step of the process includes advancing a cannulated drill 160 over the tension element, as depicted in FIG. 18. The cannulated drill may form the bone bore 18 to a depth sufficient to accept the shank 32 of the proximal anchor 30. This depth will vary depending upon the length of the shank 32. In some cases, the shank will extend across the bone to the cortical bone at the distal surface, while in the typical case the shank will only project partially into the bone. With tension maintained on the body 94 of the tension element, the proximal anchor 30 is driven into the bone using tool 50 and into locking bushing 16 of the plate 10', as illustrated in FIG. 19. This process can be repeated at a number of locations on the bone plate 10', as shown in FIG. 20. The tension at each tension element may be adjusted throughout the process, even as other tension elements are being added to the construct, to even out the plate compression on the bone or otherwise adjust the position of the plate. Once the surgeon is satisfied with the tension and orientation of all of the tension elements, the excess tension element material may be removed.

The tension element 22 is preferably a braided metal cable or similar medical grade material suitable for implantation in a patient. In the preferred embodiment, the tension element does not elongate significantly under tension. It is expected that the tensioning process may be iterative as the tension element stretches slightly as load is applied. A gauge may be used to verify the cable tension. In alternative embodiments, the tension element is formed of a more elastic material, such as a silicone rubber cord, or may incorporate a spring element with a calibrated stiffness.

In the illustrated embodiments, a single tension element is provided at each hole location in the bone plate 10/10'. Alternatively, multiple tension elements may be anchored at a common plate recess 14 or opening 14'. Each tension elements may be deployed at different angles relative to the bone plate.

The tension elements and distal anchors may be provided in a range of sizes depending upon the type of fracture being treated. For instance, the tension element may have an effective diameter of about 1-3 mm a length of 100-200 mm. The distal anchors 24, 24' and 92 may have an effective diameter of about 4-6 mm.

The size of the proximal anchors is dictated in some degree by the dimensions of the bone plate to which these anchors are fixed. For instance, the diameter of the Tinnerman washer 26 or the threaded tapered head 34 of the anchor 30 are determined by the internal diameter of the recess 14 and locking bushing 16, respectively. The height of the proximal anchors is preferably set so that the anchors do not project outside the exposed surface of the bone plate, to minimize trauma to surrounding tissue.

In the certain embodiments, the distal anchors may be integral with the tension element. In other embodiments, the distal anchors are permanently attached to the tension element in a known manner, such as by crimping or welding. It is expected, however, that the attachment between tension element and distal anchor be sufficiently strong to withstand the tension applied to the element.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

For example, the proximal anchor 30 contemplates a tapered threaded engagement between the bone plate and the anchor, via the locking bushing. Alternatively, the opening 14' in the bone plate 10' (FIG. 3) may be tapered, such as a Morse taper. The threads 36 may be eliminated on the head 34 of the proximal anchor 30 (FIGS. 3-4) so that the head 34 is a smooth tapered component, while retaining the cross-slots 38. Rather than threading the proximal anchor into the locking bushing, the tapered head may be pressed into the mating tapered opening in the bone plate while the tension element 22 is maintained in tension. With this alternative embodiment, the driving lugs 42 may also be eliminated. The driving tool 50 may be replaced with a cannulated impact driver. In order to retain the polyaxial or variable angle capability, the locking bushing may incorporate the complementary mating angle for press-fit engagement with the tapered head of the modified proximal anchor. The plate opening 14' may then retain its spherical inner surface to mate with the spherical outer surface of the bushing at a range of angles relative to the plate.

What is claimed is:

1. A system for positioning an elongated element within a bone, the system comprising:
   a first elongated element configured to extend through a bone so that a distal end of the first elongated element extends outside the bone;
   a second elongated element including a tension cable, the second elongated element having a proximal end configured to mate with the distal end of the first elongated element; and
   an exchange tool comprising a barrel defining an elongated bore open between opposing ends and sized to receive at least a portion of the first and second elongated elements, wherein the exchange tool is configured to push the second elongated element into the bone while maintaining the distal end of the first elongated element in mating contact with the proximal end of the second elongated element.

2. The system of claim 1, wherein the exchange tool further comprises:
   a first side opening defined in the barrel and communicating with the elongated bore;
   a second side opening defined in the barrel and communicating with the elongated bore, the second side opening angularly offset relative to the first side opening; and
   an intermediate side opening defined in the barrel and communicating with the elongated bore, the intermediate side opening communicating between the first and second side openings,
   wherein the first and second side openings are sized to permit removal of one of the elongated elements from the elongated bore.

3. The system of claim 1, wherein the proximal end of the second elongated element defines a recess and the distal end of the first elongated element comprises a tip configured to be received within the recess.

4. The system of claim 3, wherein the first elongated element comprises a stylet having a sharpened tip at its distal end.

5. The system of claim 3, wherein the first elongated element comprises a K-wire having a sharpened tip at its distal end.

6. The system of claim 1, wherein the barrel of the exchange tool provides a mechanism for aligning the first and second elongated elements.

7. The system of claim 6, wherein the exchange tool is configured to guide the second elongated element when it is pushed into the bone.

8. The system of claim 1, further comprising a bone plate configured to bear against a proximal surface of the bone.

9. The system of claim 8, further comprising a proximal anchor configured to secure the proximal end of the second elongated element to the bone plate.

10. The system of claim 1, wherein the second elongated element comprises a tension element with a distal anchor coupled to a distal end of the tension element, the distal anchor being incapable of passing through a bone opening.

11. The system of claim 1, wherein the barrel of the exchange tool includes an insertion portion that is sized and configured for percutaneous insertion into the body of a patient.

12. A system for positioning tension elements within a bone, the system comprising:
- a first elongated element configured to extend through a bone so that a distal end of the first elongated element extends outside the bone;
- a second elongated element including a tension element, the tension element having a proximal end and a distal end, the proximal end configured to mate with the distal end of the first elongated element; and
- an exchange tool comprising a barrel defining an elongated bore open between opposing ends and sized to receive and align at least a portion of the first and second elongated elements; and
- a distal anchor coupled to the distal end of the tension element, the distal anchor being incapable of passing through a bone opening,
- wherein the proximal end of the second elongated element defines a recess and the distal end of the first elongated element is configured to be received within the recess.

13. The system of claim 12, wherein the exchange tool is configured to push the second elongated element into the bone while maintaining the distal end of the first elongated element in mating contact with the proximal end of the second elongated element.

14. The system of claim 12, wherein the exchange tool further comprises:
- a first side opening defined in the barrel and communicating with the elongated bore;
- a second side opening defined in the barrel and communicating with the elongated bore, the second side opening angularly offset relative to the first side opening; and
- an intermediate side opening defined in the barrel and communicating with the elongated bore, the intermediate side opening communicating between the first and second side openings,
- wherein the first and second side openings are sized to permit removal of one of the elongated elements from the elongated bore.

* * * * *